US012778771B2

(12) United States Patent
Hwang et al.

(10) Patent No.: US 12,778,771 B2
(45) Date of Patent: Nov. 3, 2026

(54) NERVE CONDUIT FOR PROMOTING AMPUTATED NERVE REGENERATION USING ELECTRIC FIELDS

(71) Applicant: ENERGY MINING Co., Ltd., Suwon-si (KR)

(72) Inventors: Joon Ha Hwang, Suwon-si (KR); Young Wook Chung, Suwon-si (KR); Jang Mook Jeong, Suwon-si (KR); Hyun Moon Park, Gunpo-si (KR)

(73) Assignee: ENERGY MINING Co., Ltd., Suwon-si (KR)

( * ) Notice: Subject to any disclaimer, the term of this patent is extended or adjusted under 35 U.S.C. 154(b) by 441 days.

(21) Appl. No.: 18/392,052

(22) Filed: Dec. 21, 2023

(65) Prior Publication Data

US 2025/0082481 A1 Mar. 13, 2025

(30) Foreign Application Priority Data

Sep. 13, 2023 (KR) ........................ 10-2023-0121866

(51) Int. Cl.

| | |
|---|---|
| ***A61F 2/48*** | (2006.01) |
| ***A61F 2/00*** | (2006.01) |
| ***A61L 27/26*** | (2006.01) |
| ***A61L 27/38*** | (2006.01) |
| ***H02N 1/04*** | (2006.01) |

(52) U.S. Cl.

CPC .............. *A61F 2/482* (2021.08); *A61L 27/26* (2013.01); *A61L 27/3834* (2013.01); *H02N 1/04* (2013.01); *A61F 2002/0086* (2013.01); *A61F 2210/0004* (2013.01); *A61F 2210/0076* (2013.01); *A61F 2220/005* (2013.01); *A61F 2230/0069* (2013.01); *A61F 2250/006* (2013.01); *A61L 2430/32* (2013.01)

(58) Field of Classification Search

None

See application file for complete search history.

(56) References Cited

U.S. PATENT DOCUMENTS 4,308,868 A * 1/1982 Jhabvala ................ A61N 1/372 607/72
2013/0317582 A1* 11/2013 Chen ......................... A61F 7/12 607/116
2019/0321644 A1* 10/2019 Maharbiz ........... A61N 1/37282

(Continued)

FOREIGN PATENT DOCUMENTS

KR 10-2012-0084903 A 7/2012
KR 10-1860230 B1 5/2018

(Continued)

*Primary Examiner* — Michael W Kahelin

(74) *Attorney, Agent, or Firm* — Studebaker Brackett PLLC

(57) ABSTRACT

Disclosed is a nerve conduit. The nerve conduit includes: a conduit body which connects both sides of a severed nerve within a biological body; a triboelectric nanogenerator which includes an upper friction layer and a lower friction layer; a multilinear electrode which is located between the conduit body and the triboelectric nanogenerator, and is electrically connected to the upper and lower friction layers; and an upper encapsulation layer which is positioned above the triboelectric nanogenerator. The nerve conduit of the present disclosure can enhance nerve regeneration efficiency.

11 Claims, 7 Drawing Sheets

(56) References Cited

U.S. PATENT DOCUMENTS

| | | | | |
|---|---|---|---|---|
| 2023/0093932 | A1 * | 3/2023 | Kim | A61N 1/3787<br>310/310 |
| 2025/0127512 | A1 * | 4/2025 | Srinivasan | A61L 27/50 |

FOREIGN PATENT DOCUMENTS

| | | | |
|---|---|---|---|
| KR | 10-2019-0064168 | A | 6/2019 |
| KR | 10-2022-0168455 | A | 12/2022 |
| KR | 10-2535111 | B1 | 5/2023 |

* cited by examiner

NERVE CONDUIT FOR PROMOTING AMPUTATED NERVE REGENERATION USING ELECTRIC FIELDS

CROSS-REFERENCE TO RELATED APPLICATIONS

The present application claims the benefit of priority to Korean Patent Application No. 10-2023-0121866, filed on Sep. 13, 2023, in the Korean Intellectual Property Office. The disclosures of the above-listed application are hereby incorporated by reference herein in their entirety.

BACKGROUND OF THE INVENTION

Field of the Invention

The present disclosure relates to a biodegradable nerve conduit for promoting regeneration of severed nerves utilizing an electric field and a method for manufacturing the same.

This work (Grants No. S3282292) was supported by Business for Startup growth and technological development (TIPS Program) funded Korea Ministry of SMEs and Startups in 2022

This work was supported by the Next Generation Intelligence Semiconductor Foundation Program (20025736, Development of MICS SoC and platform for invivo implantable electroceutical device) funded By the Ministry of Trade, Industry & Energy (MOTIE, Korea)"

Background Art

In cases where nerves are severed due to an accident or surgery, a surgical procedure is conducted to suture both sides of the severed nerve.

If a gap between both sides of the severed nerve is less than 5 mm, treatment can be conducted easily by suturing both sides of the severed nerve or connecting both sides of the severed nerve with a guide conduit. However, if the gap between both sides of the severed nerve is more than 5 mm, treatment to suture both sides of the severed nerve is not possible.

Therefore, if the gap between both sides of the severed nerve is more than 5 mm, treatment can be conducted using autotransplantation and guide conduits, but autotransplantation may cause damage to a nerve extraction region and cannot be used multiple times. For reference, autotransplantation means that nerves of other region of a biological body which is less used or not used are extracted, and then, directly transplanted to both sides of the severed nerve.

Recently, in place of autotransplantation, a technical development to promote the regeneration of the severed nerve by connecting both sides of the severed nerve with conductive hydrogels.

However, connecting both sides of the severed nerve with conductive hydrogels is less effective in regeneration of the severed nerve than autotransplantation, cannot not resolve biocompatibility, is unstable in electrical connection between biodegradable electrodes and the conductive hydrogels, and is difficult to form sufficient electric fields for promoting regeneration between severed nerves.

SUMMARY OF THE INVENTION

Accordingly, the present disclosure has been made to solve the above-mentioned problems occurring in the prior arts, and it is an objective of the present disclosure to provide a nerve conduit which forms a sufficient electric field for promoting regeneration between severed nerves.

It is another objective of the present disclosure to provide a method for forming an electric field in a nerve regeneration direction to promote regeneration between severed nerves.

The objectives of the present disclosure are not limited to those mentioned above, and other objectives not mentioned herein will be clearly understood by those skilled in the art from the following description.

To accomplish the above object, according to the present disclosure, there is provided a nerve conduit including: a conduit body which connects both sides of a severed nerve within a biological body; a triboelectric nanogenerator which includes an upper friction layer and a lower friction layer; a multilinear electrode which is located between the conduit body and the triboelectric nanogenerator, and is electrically connected to the upper and lower friction layers; and an upper encapsulation layer which is positioned above the triboelectric nanogenerator.

In this instance, when the triboelectric nanogenerator generates power by external ultrasonic waves, an electric field can be formed in a nerve regeneration direction through the multilinear electrode.

The conduit body can contain conductive hydrogels.

The multilinear electrode can include a first electrode, a second electrode arranged to intersect with the first electrode, and a substrate positioned below the first and second electrodes and above the conduit body.

The upper friction layer can include an upper electrode electrically connected to the first electrode and an upper friction material, the lower friction layer can include a lower electrode electrically connected to the second electrode and a lower friction material, and a lower encapsulation layer can be positioned between the lower friction layer and the multilinear electrode.

The conduit body, the upper triboelectric nanogenerator, the multilinear electrode, the upper encapsulation layer, and the lower encapsulation layer can be made of biodegradable materials.

The upper and lower encapsulation layers can contain one of poly(lactide-co-glycolide) (PLGA), poly(3-hydroxybutyric acid-co-3-hydroxyvaleric acid) (PHBV), and poly lactic acid (PLA), and the upper and lower encapsulation layers may be cracked by the application of ultrasonic waves of a reference intensity or higher.

The upper and lower friction materials can contain one of poly(lactide-co-glycolide) (PLGA), polyvinyl (PVA), poly lactic acid (PLA), and polyethylene glycol (PEG).

The upper and lower electrodes can include any one of Mg and Mo.

The upper electrode of the triboelectric nanogenerator can be positioned above the upper friction material, and a biodegradable spacer can be located between a lower portion of the upper friction material and an upper portion of the lower friction material.

The inner diameter of the conduit body and the outer diameter of the severed nerve can be combined with each other, and the combined region of the conduit body and the severed nerve can be bonded by a biodegradable adhesive.

The conduit body can include transplantation stem cells.

The conduit body, the multilinear electrode, and the triboelectric nanogenerator can be each manufactured separately, the multilinear electrode and the triboelectric nanogenerator can be primarily combined with each other, and then, the conduit body and the multilinear electrode can be secondarily combined with each other.

Other detailed matters of the present disclosure will be included in detailed description and drawings.

The nerve conduit according to the present disclosure can promote regeneration of the severed nerve by effectively transmitting electrical signals to the severed nerve, and form an electric field in the nerve regeneration direction to promote regeneration between the severed nerves.

The advantages of the present disclosure are not limited to the above-mentioned advantages, and other advantages, which are not specifically mentioned herein, will be clearly understood by those skilled in the art from the following description.

DETAILED DESCRIPTION OF THE PREFERRED EMBODIMENT

Figure 1:
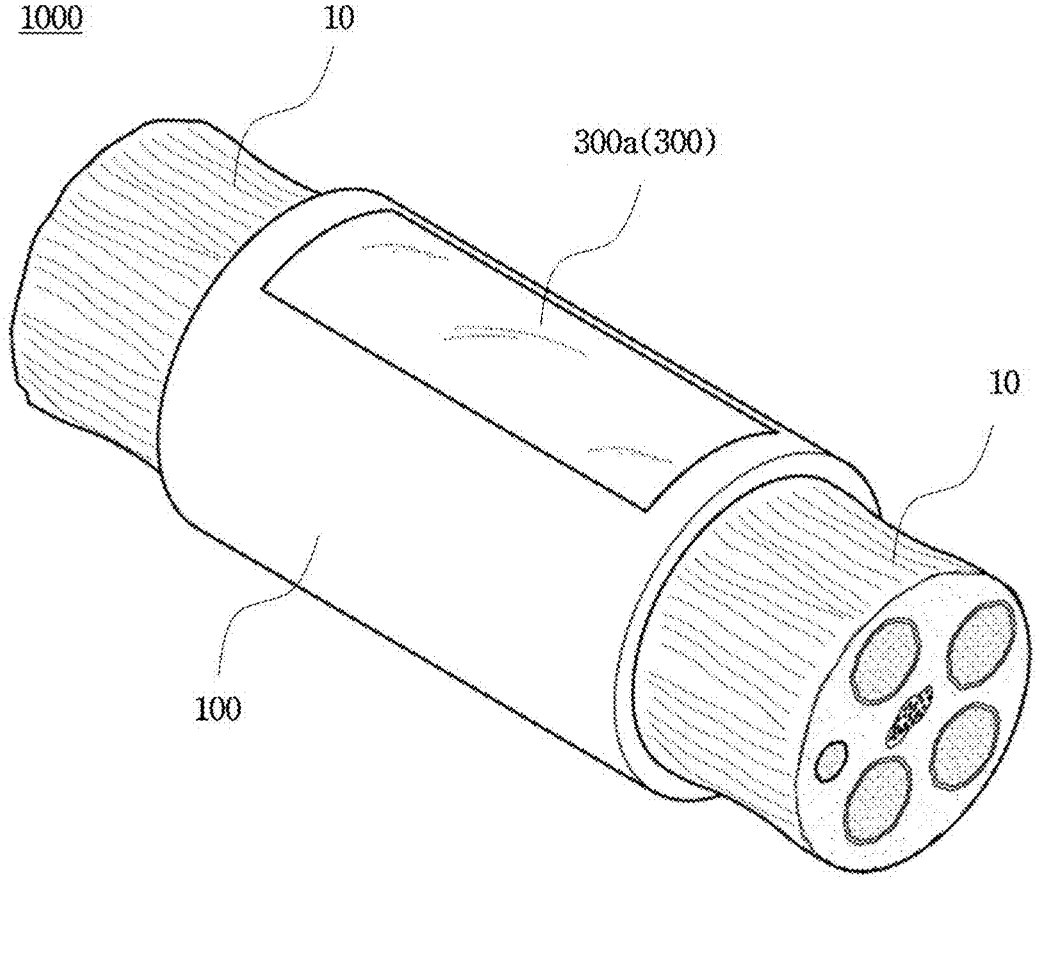
FIG. 1 is a perspective view of a nerve conduit according to the present disclosure.

The present disclosure can be modified in various forms and can have various embodiments, and specific embodiments will be illustrated in the drawings and described in detail. Advantages and features of the present disclosure and methods accomplishing the advantages and features will become apparent from the following detailed description of exemplary embodiments with reference to the accompanying drawings. However, the present disclosure is not limited to exemplary embodiment disclosed herein but will be implemented in various forms.

In the following embodiments, terms such as 'first,' 'second,' etc., are used not in a limiting sense but to distinguish one component from another.

In the following embodiments, a singular expression includes a plural expression unless a description to the contrary is specifically pointed out in context In the following embodiments, terms like 'comprising' or 'having' mean that the features or components described in the specification exist, without precluding the possibility of one or more other features or components being added.

In the following embodiments, when it is said that an area or a component is 'on' or 'above' another part, it includes not only being directly on top of the other part but also having other areas or components intervening in between.

In the drawings, for convenience of description, components may be exaggerated or reduced in size. For example, the size and thickness of each component shown in the drawings are arbitrarily shown for convenience of description, and the present disclosure is not limited thereto.

In some embodiments, a specific process order can be performed differently from the order described. For example, two processes described in succession can be performed substantially simultaneously or in the reverse order of the described one.

In this specification, "A and/or B" indicates A, B, or both A and B. In the same way, "at least one of A and B" indicates A, B, or both A and B.

In the following embodiments, when it is mentioned that areas or components are connected, it means that the areas or the components are directly connected and/or that the areas or the components are indirectly connected with other areas or components intervening. For example, in this specification, when it is said that areas or components are 'electrically connected,' it indicates that they are directly electrically connected, and/or indirectly electrically connected through other areas or components intervening.

Hereinafter, embodiments of the present disclosure are described in detail with reference to the accompanying drawings.

Figure 2:
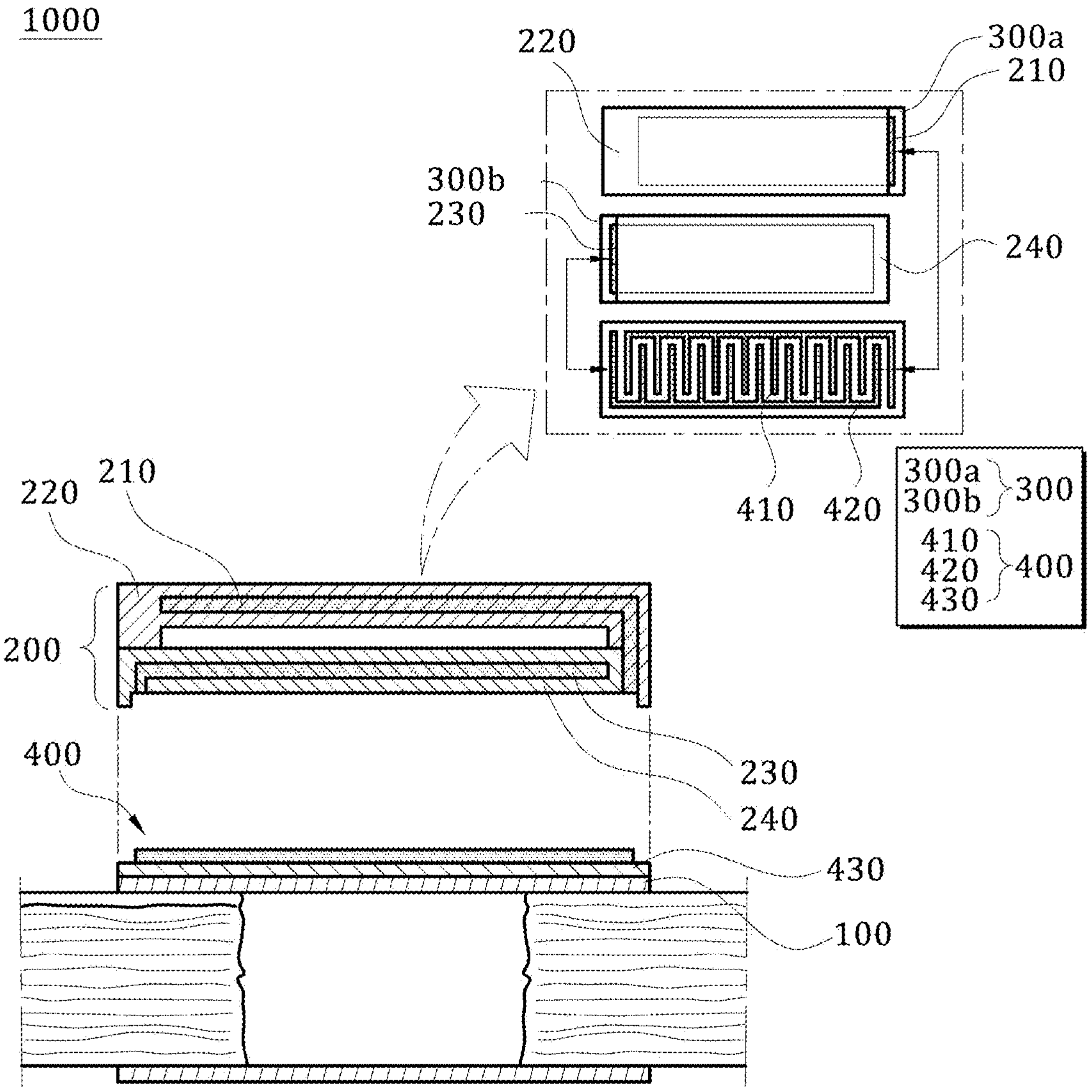
FIG. 2 is a cross-sectional view of the nerve conduit according to the present disclosure and a plan view of a portion of the nerve conduit.

FIG. 1 is a perspective view of a nerve conduit 1000 according to the present disclosure. FIG. 2 is a cross-sectional view of the nerve conduit 1000 according to the present disclosure and a plan view of a portion of the nerve conduit 1000.

The nerve conduit 1000 may include a conduit body 100, a triboelectric nanogenerator 200, an encapsulation layer 300 which includes an upper encapsulation layer **300*a* and a lower encapsulation layer 300*b*, and a multilinear electrode 400. Here, at least one of the conduit body 100, the triboelectric nanogenerator 200, the encapsulation layer 300, and the multilinear electrode 400** can be made of a biodegradable material.

In an embodiment, the conduit body 100 and the triboelectric nanogenerator 200 may be made of a biodegradable material that has a faster biodegradation rate than the encapsulation layer 300 (**300*a* and 300*b***).

The conduit body 100 can serve to connect both sides of a severed nerve 10 within a biological body.

In an embodiment, the conduit body 100 can be formed in a ring shape, may have an inner diameter corresponding to the outer diameter of the severed nerve 10, and the outer diameter of the severed nerve 10 and the inner diameter of the conduit body 100 can be combined. That is, both sides of the severed nerve 10 can be inserted into both sides of the conduit body 100.

In an embodiment, the conduit body 100 can include a conductive hydrogels, and may include conductive fillers. The conductive hydrogels included in the conduit body 100 can serve to electrically connect both sides of the severed nerve 10.

Additionally, the conductive hydrogels included in the conduit body 100 can have mechanical properties similar to those of nerves, thereby minimizing fatigue of the nerves, and making it easy for nerve regeneration-promoting substances like ionic cells to infiltrate due to the permeability. Additionally, when both sides of the severed nerve 10 are electrically connected through the conductive hydrogels included in the conduit body 100, the regeneration of the severed nerve 10 can be activated by the minute electromotive force (for example, less than 100 mv) of the severed nerve 10. However, the activation of the regeneration of the severed nerve 10 by the minute electromotive force of the severed nerve 10 does not mean promotion of regeneration of the severed nerve 10.

In an embodiment, the conductive hydrogels included in the conduit body 100 may be any one of GelMa, chitosan, collagen, and PVA, and salts or conductive fillers may be added to enhance conductivity.

The conductive fillers included in the conduit body 100 can adjust the impedance of the conduit body 100 depending on the amount contained in the conduit body 100. For example, if 1 wt % of conductive fillers are contained in the conduit body 100, the impedance of the conduit body 100 may be 100 kohm, and if 2 wt % of conductive fillers are contained, the impedance of the conduit body 100 may be 50 kohm. Through the above, the amount of conductive fillers contained in the conduit body 100 can be adjusted so that the impedance of the conduit body 100 corresponds to the optimal impedance of the triboelectric nanogenerator 200, thereby allowing the conduit body 100 to be customized to the triboelectric nanogenerator 200.

In an embodiment, the conduit body 100 may further include poly(lactide-co-glycolide) (PLGA). Therefore, the conduit body 100 may be cracked upon application of ultrasonic waves with strength above a reference level. At this time, as a body fluid of the biological body penetrates into the conduit body 100 through the cracks occurred in the conduit body 100, the biodegradation of the conduit body 100 can proceed. Here, the reference intensity of the ultrasonic waves may be 3 W/cm2, but the embodiment is not limited thereto.

Furthermore, at least one enzyme selected from proteinase K, lipase, and lysozyme can be accommodated between the conduit body 100 and the encapsulation layer 30 (300*a* and 300*b*). If at least one enzyme selected from proteinase K, lipase, and lysozyme is accommodated between the conduit body 100 and the encapsulation layer 30 (300*a* and 300*b*), at least one enzyme among proteinase K, lipase, and lysozyme is dissolved by the body fluid of the biological body that has penetrated into the conduit body 100 through the cracks, and the dissolved enzyme among proteinase K, lipase, and lysozyme can act as an enzyme that accelerates the biodegradation of the nerve conduit 1000.

The triboelectric nanogenerator 200 can be electrically connected to the severed nerve 10 through the conduit body 100, thereby transmitting an electrical signal generated by the application of ultrasonic waves to the severed nerve 10. As a result, the electrical signal transmitted from the triboelectric nanogenerator 200 to the severed nerve 10 can promote the regeneration of the severed nerve 10.

For reference, the triboelectric nanogenerator 200 can transmit the triboelectricity generated based on friction by the application of ultrasonic waves to the severed nerve 10, and the triboelectricity can be an electrical signal.

Figure 6:
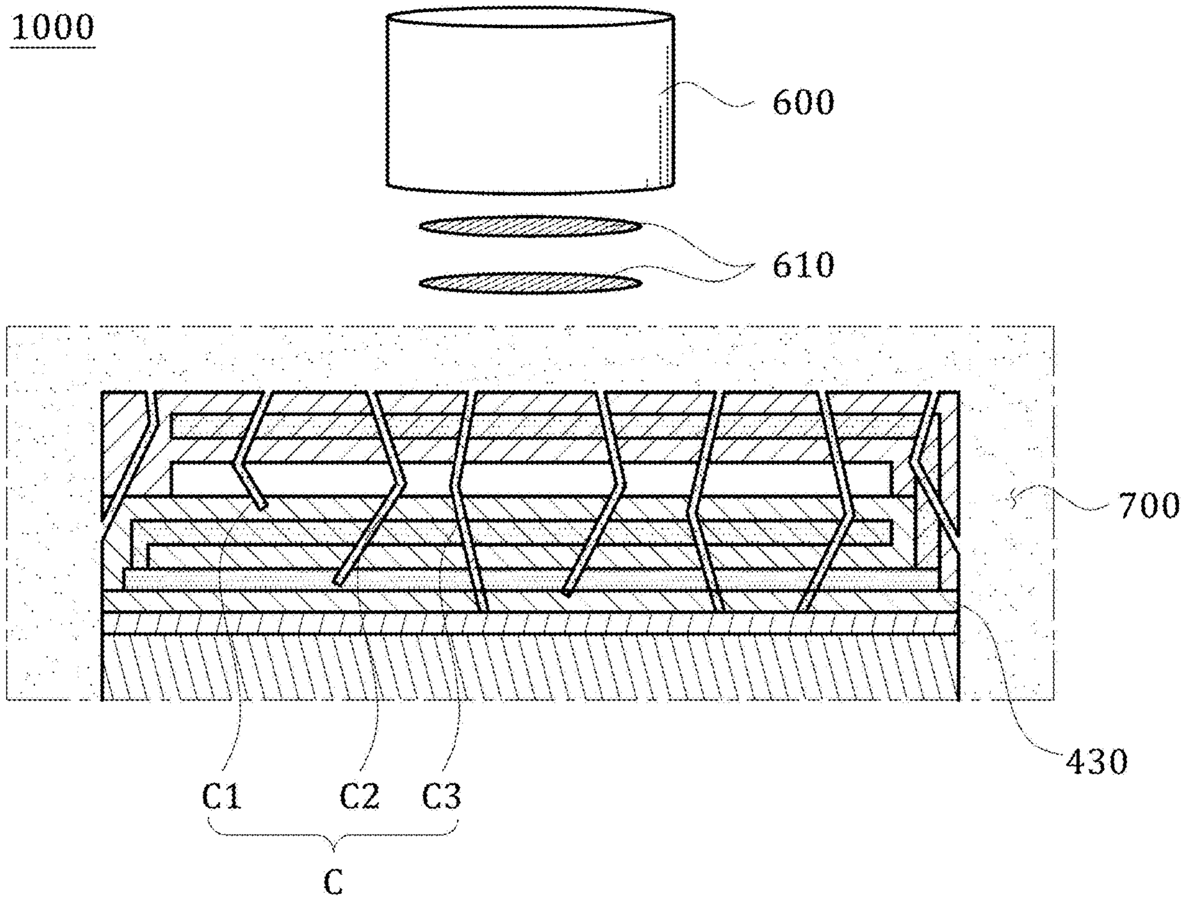
FIG. 6 is a diagram for depicting the nerve conduit that a crack is generated due to application of ultrasonic waves of a reference intensity or higher from external ultrasonic waves.

In an embodiment, the ultrasonic waves applied to the triboelectric nanogenerator 200 may be generated by an ultrasonic generator 600 (see FIG. 6). The ultrasonic generator 600 can set the intensity of the ultrasonic waves applied to the triboelectric nanogenerator 200, and the timing of applying the ultrasonic waves to the triboelectric nanogenerator 200 can be set.

In an embodiment, the triboelectric nanogenerator 200 may have a curved plate shape having a radius corresponding to the radius of the conduit body 100. Additionally, the triboelectric nanogenerator 200 may have an annular shape corresponding to the form of the circumference of the conduit body 100.

The triboelectric nanogenerator 200 may include upper friction layers 210 and 220 and lower friction layers 230 and 240, wherein the upper friction layers 210 and 220 may include an upper electrode 210 and an upper friction material 220, and the lower friction layers 230 and 240 may include a lower electrode 230 and a lower friction material 240.

Here, the upper friction material 220 and the lower friction material 240 may be any one of poly(lactide-co-glycolide) (PLGA), polyvinyl alcohol (PVA), poly lactic acid (PLA), and polyethylene glycol (PEG), but the embodiment is not limited thereto.

The upper encapsulation layer 300*a* may be placed above the upper electrode 210, and the lower encapsulation layer 300*b* may be positioned below the lower electrode 230.

That is, the upper encapsulation layer 300*a* is located above the triboelectric nanogenerator 200, and the lower encapsulation layer 300*b* may be positioned between the lower friction layer 240 and the multilinear electrode 400.

The upper and lower encapsulation layers 300*a* and 300*b* may contain any one of PLGA, PHBV, and PLA, and the upper and lower encapsulation layers 300*a* and 300*b* 300 may be cracked by application of ultrasonic waves with strength above the reference level.

The upper and lower electrodes 210 and 230 may include any one of Mg and Mo. The upper electrode 210 is positioned above the upper friction material 220, and a biodegradable spacer may be added below the upper friction material and above the lower friction material. The multilinear electrode 400 is positioned between the conduit body 100 and the triboelectric nanogenerator 200, and may be electrically connected to the upper friction layers 210 and 220 and the lower friction layers 230 and 240.

The multilinear electrode 400 includes a first electrode 410 and a second electrode 420 arranged to intersect with the first electrode 410, and may include a substrate 430 positioned below the first and second electrodes 410 and 420 and above the conduit body 100. The first electrode 410 and the second electrode 420 may have a trench shape and may be arranged to intersect (alternate) without touching as illustrated in FIG. 2.

The first electrode 410 of the multilinear electrode 400 may be electrically connected to the upper electrode 210, and the second electrode 420 may be electrically connected to the lower electrode 230.

Figure 3:
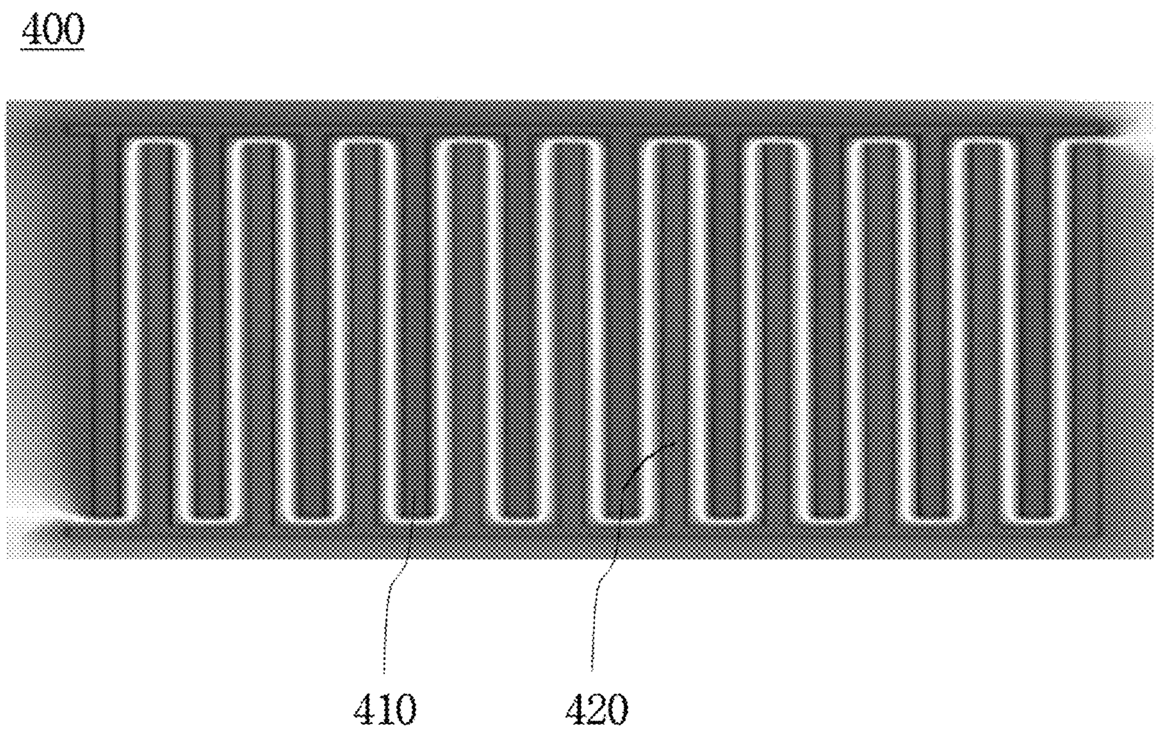
FIG. 3 is a view visually representing an electric field distribution in a multilinear electrode when power is generated by a triboelectric nanogenerator by external ultrasonic waves according to the present disclosure.

FIG. 3 is a diagram visually illustrating the electric field distribution of the multilinear electrode 400 when power is generated by the triboelectric nanogenerator 200 due to external ultrasonic waves.

Referring to FIG. 3, due to the structural features of the multilinear electrode 400, an electric field generated by the triboelectric nanogenerator 200 can be applied along the nerves across the entire range of the nerve severance region.

At this time, the electric field formed by the structural features of the multilinear electrode 400 overcomes the limitations of the conventional art where the electric field is formed in the vertical direction of the nerves, and can be formed in the direction of nerve regeneration direction (horizontal direction of the nerves, proximal to distal or distal to proximal). Consequently, the voltage applied conventionally was measured between −1V to 1V over time, but due to the structural features and arrangement of the multilinear electrode 400 disclosed herein, a voltage value between −1.5V to 1.5V can be measured, so the multilinear electrode 400 according to the present disclosure is more excellent in promotion of nerve regeneration than the conventional art. Here, 'Distal' refers to a location farther from the original damage region, and 'Proximal' means closer to the damage region.

Furthermore, the application of the multilinear electrode 400 can overcome the limitations when the multilinear electrode is not applied (namely, nerve regeneration promotion by the electric field decreases as the length of nerve severance increases).

Figure 4:
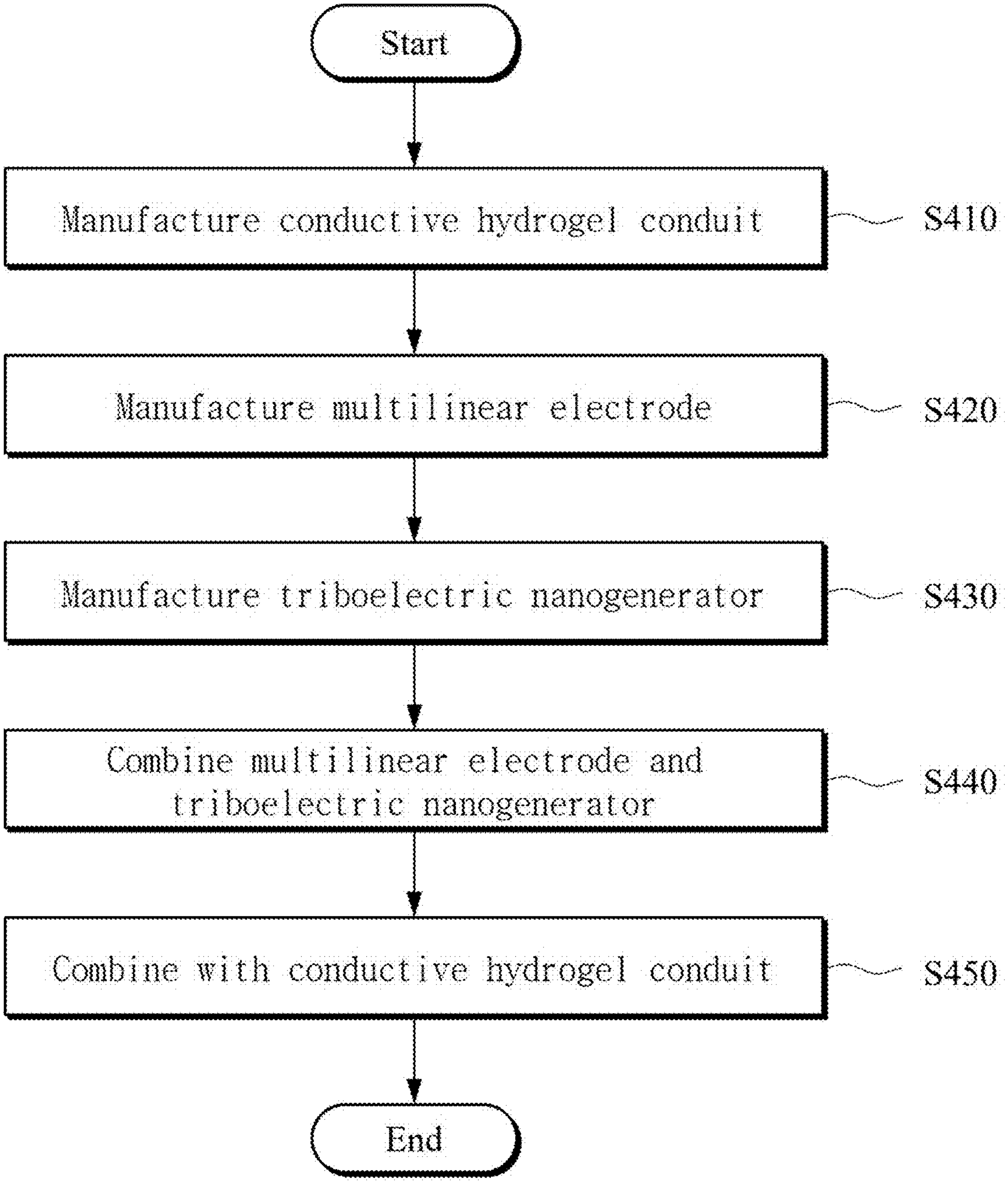
FIG. 4 is a sequence diagram illustrating a process of manufacturing the nerve conduit according to the present disclosure.

FIG. 4 is a sequence diagram illustrating a process of manufacturing a nerve conduit 1000 according to the present disclosure.

According to the present disclosure, the conduit body 100, the multilinear electrode 400, and the triboelectric nanogenerator 200 can each be manufactured separately, and a nerve conduit 1000 can be produced through the combination of the components. The manufacturing method is more time-effective in measuring voltage than the conventional art of sequentially stacking detailed components, thereby enabling more effective nerve regeneration.

The manufacturing process of the nerve conduit 1000 is as follows. First, the conduit body 100 is made of conductive hydrogels (Step S410). Next, the multilinear electrode can be manufactured (Step S420). At this time, a mask may be attached onto the biodegradable substrate 430, and an electrode of 200 to 300 nm can be deposited using an e-beam evaporator.

After the step S420, the triboelectric nanogenerator 200 is produced (Step S430), and the multilinear electrode 400 and the triboelectric nanogenerator 200 can be primarily combined with each other (Step S440). Thereafter, the conduit body 100 and the multilinear electrode 400 are secondarily combined with each other to finally produce the nerve conduit 1000 (Step S450).

Here, the multilinear electrode 400 and the triboelectric nanogenerator 200 can be combined using hot pressing (the primary combination), but the embodiment is not limited thereto. The conduit body 100 and the multilinear electrode 400 can be combined with each other through a biodegradable adhesive (the secondary combination), but the embodiment is not limited thereto.

Applying the method of manufacturing the nerve conduit 1000 according to the present disclosure can significantly overcome the limitations of the conventional art (since the friction layer, the spacer, and the encapsulation layer are manufactured on the conduit body in a stacking manner, it is difficult to uniformly attach each layer on the curved conduit body, and the output of the triboelectric nanogenerator is reduced).

Figure 5:
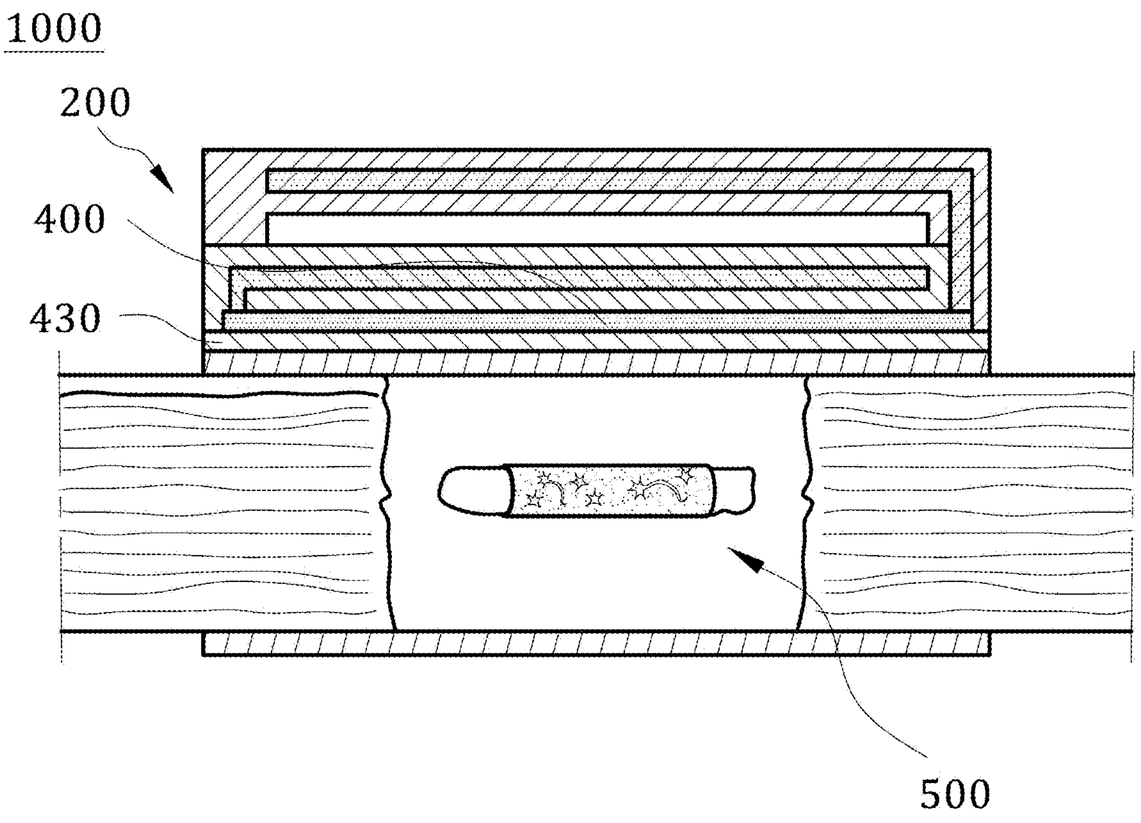
FIG. 5 is a diagram for depicting the nerve conduit implanted with stem cells according to the present disclosure.

FIG. 5 is a diagram for depicting the nerve conduit 1000 with transplanted stem cells 500 according to the present disclosure.

When stem cells 500 are transplanted inside the conduit body 100, the electrical field therapy generated by the triboelectric nanogenerator 200 and an additional nerve regeneration effect can be derived.

Accordingly, when stem cells for transplantation are transplanted in the conduit body 100, the electrical signals is transferred to the severed nerve 10 from the triboelectric nanogenerator 200 through the conduit body 100 to promote the regeneration of the severed nerve 10. When the regeneration of the severed nerve 10 is promoted, the therapeutic effect of the stem cells is added, thereby further promoting the regeneration of the severed nerve 10. The stem cells for transplantation can be implanted on the inner surface of the conduit body 100.

FIG. 6 is a diagram for depicting the nerve conduit 1000 where cracks occur due to the application of ultrasonic waves of a reference intensity or higher from an external ultrasonic waves. The external ultrasonic waves can be generated by an ultrasonic generator 600.

In an embodiment, the encapsulation layer 300, the triboelectric nanogenerator 200, the multilinear electrode 400, etc., being made of biodegradable materials, can be cracked (C1 to C3) by the application of ultrasonic waves of the reference intensity or higher, and as a body fluid of the biological body penetrates, the biodegradation of the conduit body 100 can proceed. Here, the reference intensity of the ultrasonic waves may be 3 W/cm2, but the embodiment is not limited thereto.

Here, enzymes that accelerate biodegradation may be added inside the conduit body 100 to facilitate faster degradation. Before strong ultrasonic waves are irradiated, the encapsulation layer protects the device to prevent infiltration of body liquid, but the encapsulation layer may be cracked by the strong ultrasonic waves. Additionally, if enzymes embedded within the friction material exist, biodegradable friction materials may be activated while being melted by the body liquid.

That is, when high-intensity ultrasonic waves are irradiated, the encapsulation layer may be cracked, the body liquid into the device may flow in through the cracks, and the decomposition of the device may be accelerated through internal enzymes.

Figure 7:
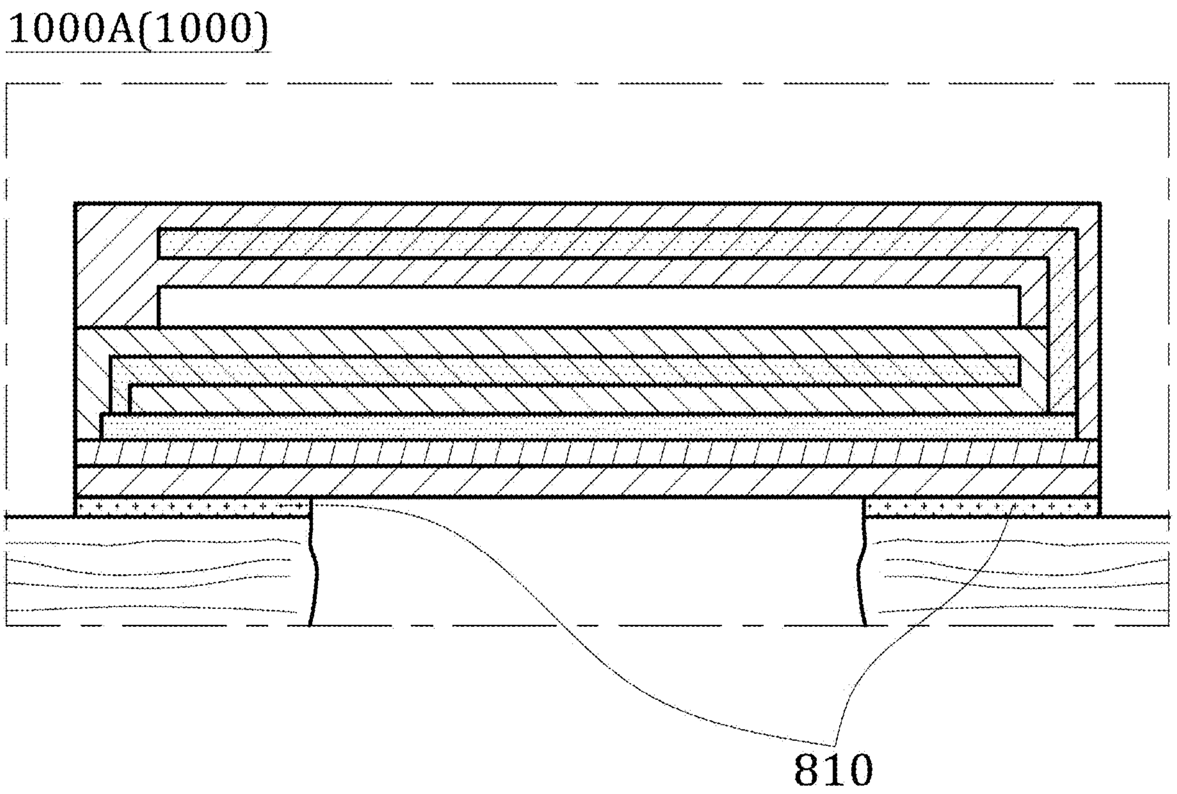
FIG. 7 is a diagram for depicting a method of bonding nerves and a conduit body using a biodegradable adhesive according to the present disclosure.

FIG. 7 is a diagram for depicting a method of bonding nerves and a conduit body using a biodegradable adhesive 810 according to the present disclosure.

Here, the biodegradable adhesive 810 may be a naturally derived material such as chitosan, collagen, etc., may be produced by binding functional groups such as catechol, galloyl, etc., to synthetic materials such as GelMa, PVA, PEG, or may be produced by mixing with plant-derived polyphenols like tannic acid, but the embodiment is not limited thereto.

Additionally, the application of the biodegradable adhesive 810 can overcome the limitations of the conventional art that requires delicate surgery using surgical sutures for fixation.

As described above, while the present invention has been particularly shown and described with reference to the example embodiments thereof, it will be understood by those of ordinary skill in the art that the disclosure may be embodied in other concrete forms without changing the technological scope and essential features. Therefore, the above-described embodiments should be considered only as examples in all aspects and not for purposes of limitation.

What is claimed is:

1. A nerve conduit comprising:

a conduit body configured to connect both sides of a severed nerve within a biological body;

a triboelectric nanogenerator which includes an upper friction layer and a lower friction layer;

a multilinear electrode which is located between the conduit body and the triboelectric nanogenerator, and is electrically connected to the upper and lower friction layers; and an upper encapsulation layer which is positioned above the triboelectric nanogenerator, wherein the multilinear electrode includes a first electrode, a second electrode arranged to intersect with the first electrode, and a substrate positioned below the first and second electrodes and above the conduit body, wherein the upper friction layer includes an upper electrode electrically connected to the first electrode and an upper friction material, wherein the lower friction layer includes a lower electrode electrically connected to the second electrode and a lower friction material, and wherein a lower encapsulation layer is positioned between the lower friction layer and the multilinear electrode.

2. The nerve conduit according to claim 1, wherein when the triboelectric nanogenerator generates power by external ultrasonic waves, an electric field is formed in a nerve regeneration direction through the multilinear electrode.

3. The nerve conduit according to claim 2, wherein the conduit body contains a conductive hydrogel.

4. The nerve conduit according to claim 1, wherein the conduit body, the upper triboelectric nanogenerator, the multilinear electrode, the upper encapsulation layer, and the lower encapsulation layer are made of biodegradable materials.

5. The nerve conduit according to claim 4, wherein the upper and lower encapsulation layers contain one of poly (lactide-co-glycolide) (PLGA), poly(3-hydroxybutyric acid-co-3-hydroxyvaleric acid) (PHBV), and poly lactic acid (PLA), and wherein the upper and lower encapsulation layers are configured to be cracked by the application of ultrasonic waves of a reference intensity or higher.

6. The nerve conduit according to claim 5, wherein the upper and lower friction materials contain one of poly (lactide-co-glycolide) (PLGA), polyvinyl alcohol (PVA), poly lactic acid (PLA), and polyethylene glycol (PEG).

7. The nerve conduit according to claim 6, wherein the upper and lower electrodes include any one of Mg and Mo.

8. The nerve conduit according to claim 7, wherein the upper electrode of the triboelectric nanogenerator is positioned above the upper friction material, and wherein a biodegradable spacer is located between a lower portion of the upper friction material and an upper portion of the lower friction material.

9. The nerve conduit according to claim 8, wherein the inner diameter of the conduit body is configured to be combined with the outer diameter of the severed nerve, and the inner diameter of the conduit body is configured to be bonded with the outer diameter of the severed nerve by a biodegradable adhesive.

10. The nerve conduit according to claim 9, wherein the conduit body includes transplantation stem cells.

11. The nerve conduit according to claim 5, wherein the conduit body, the multilinear electrode, and the triboelectric nanogenerator are each manufactured separately, the multilinear electrode and the triboelectric nanogenerator are primarily combined with each other, and then, the conduit body and the multilinear electrode are secondarily combined with each other.

* * * * *